United States Patent [19]

Cook et al.

[11] Patent Number: 4,893,636
[45] Date of Patent: Jan. 16, 1990

[54] MEDICAL CONTAINER STOPPER

[75] Inventors: Boyce W. Cook, Deland, Fla.; William R. Fiehler, St. Louis, Mo.

[73] Assignee: Sherwood Medical Company, St. Louis, Mo.

[21] Appl. No.: 165,806

[22] Filed: Mar. 9, 1988

[51] Int. Cl.$^4$ .............................................. A61M 5/18
[52] U.S. Cl. ..................... 128/764; 604/205; 215/247; 215/296
[58] Field of Search ............... 128/760, 762–766, 128/771; 604/38, 201, 205, 231–235, 239; 215/296, 355, 307, 247; 220/DIG. 19

[56] References Cited

U.S. PATENT DOCUMENTS

| | | |
|---|---|---|
| 2,812,231 | 11/1957 | Zar . |
| 3,136,440 | 6/1964 | Krug et al. ............... 128/764 X |
| 3,141,460 | 7/1964 | Tsuchatzopoulos ........ 604/201 X |
| 3,659,587 | 5/1972 | Baldwin ..................... 128/764 |
| 3,695,478 | 10/1972 | Sie et al. .................. 604/201 X |
| 3,817,240 | 6/1974 | Ayres ........................ 604/205 X |
| 3,898,046 | 8/1975 | Ikeda et al. . |
| 3,931,815 | 1/1976 | Takatsuki ................... 604/205 X |
| 3,958,572 | 5/1976 | Lawhead . |
| 3,974,930 | 8/1976 | Gizard et al. . |
| 4,150,666 | 4/1979 | Brush ......................... 128/763 |
| 4,154,229 | 5/1979 | Nugent ....................... 128/764 |
| 4,202,334 | 5/1980 | Elson . |
| 4,444,330 | 4/1984 | Kasai et al. . |
| 4,465,200 | 8/1984 | Percarpio . |
| 4,488,656 | 12/1984 | Fukuoka et al. . |
| 4,576,595 | 3/1986 | Aas et al. .................. 128/763 X |

FOREIGN PATENT DOCUMENTS 1345979 2/1974 United Kingdom .............. 128/764

Primary Examiner—Angela D. Sykes
Attorney, Agent, or Firm—Andrew J. Beck; Montgomery W. Smith; Charles Smith

[57] ABSTRACT

A stopper for medical containers such as blood collection tubes having integral flange and plug portions, the flange portion being substantially larger in diameter than the plug portion, which plug portion is sized to sealably close the container. The stopper has opposed wells formed in the flange and plug portions, the well in the flange portion having a relatively flat bottom surface at least as large in diameter as the diameter of the opposed well in the plug portion. The flange portion is constructed to be guided into a tube holder into which it is inserted such that one end of a needle projecting into the interior of the tube holder will penetrate the stopper in the area of the opposed wells so as to avoid otherwise contacting the stopper. The enlarged flange portion also serves to facilitate removal of the stopper from the container without contaminating a handler.

8 Claims, 1 Drawing Sheet

U.S. Patent  Jan. 16, 1990  4,893,636
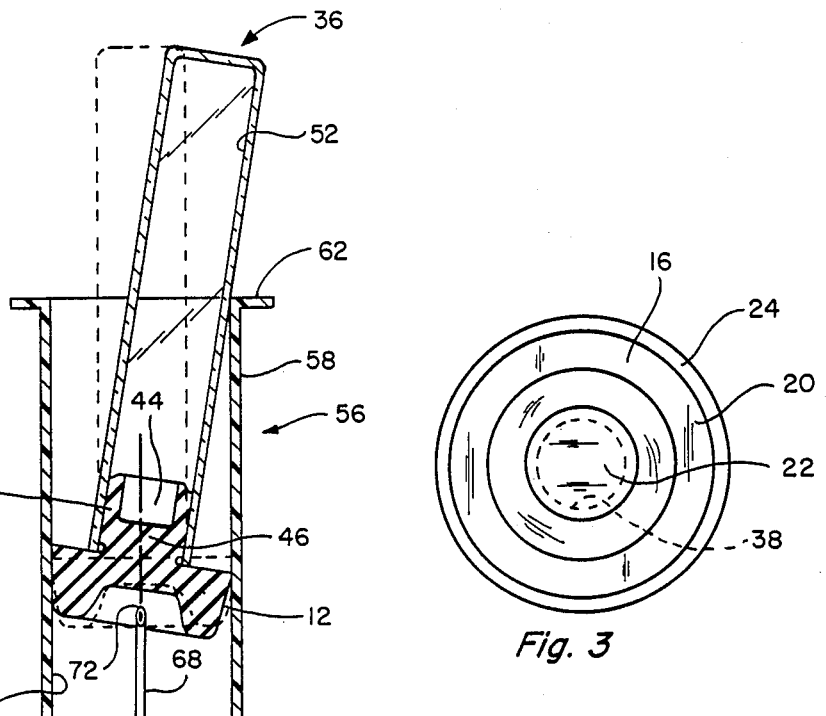
Fig. 3
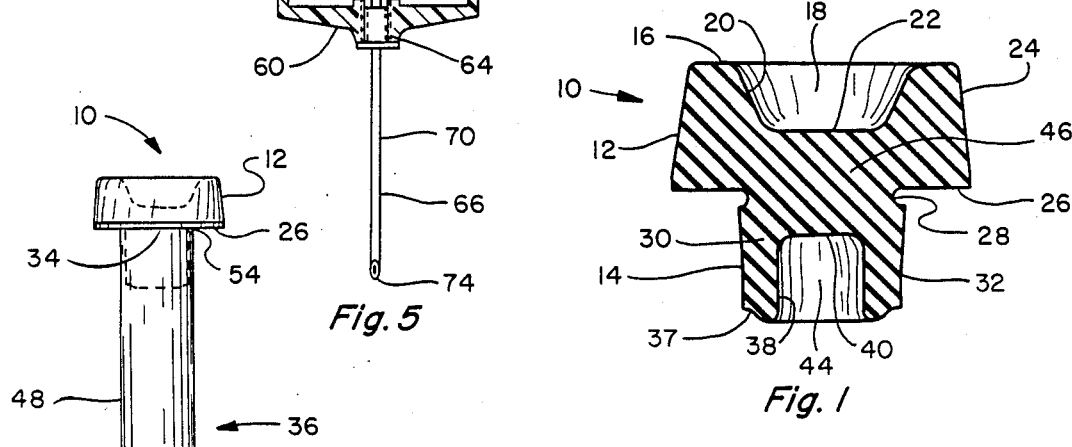
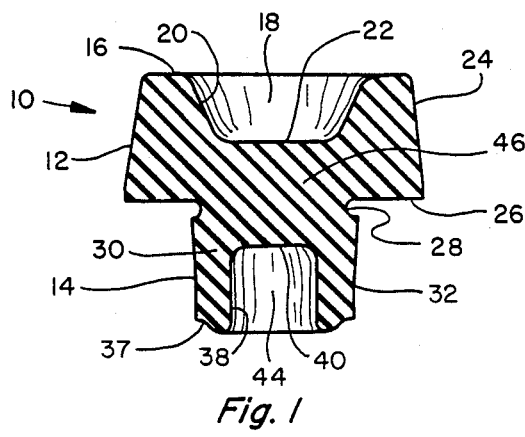
Fig. 1
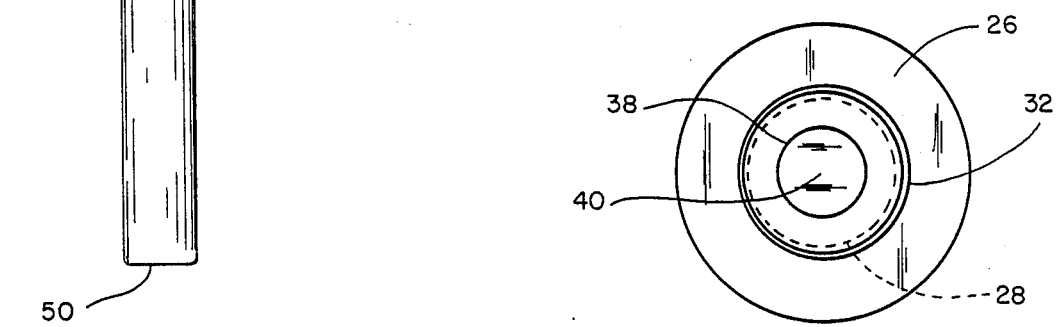
Fig. 4  Fig. 5
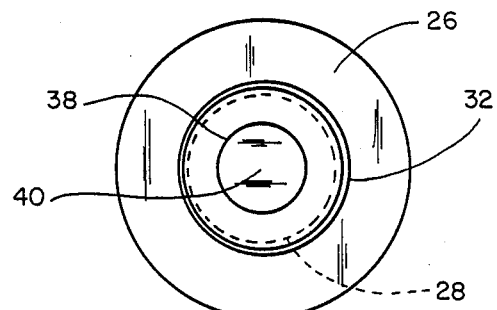
Fig. 2

MEDICAL CONTAINER STOPPER

BACKGROUND OF THE INVENTION

This invention relates to stoppers for medical containers and, more particularly, to stoppers for blood collection tubes and the like which enable the use of such collection tubes with oversized tube holders.

The most common sealed fluid sample containers are sealed and evacuated blood sample collection tubes used for receiving and preserving for testing samples of fluid blood. When drawing or collecting blood samples sealed and partially evacuated glass collection tubes are frequently used with a tube holder sized to receive collection tubes having their stoppers in place. The tube holder also generally includes a needle cannula extending axially therefrom. In order to permit blood to pass into the collection tube, the stopper is inserted into the tube holder and one end of the double-ended needle or the like punctures and holds the stopper and collection tube in place until the desired volume of blood sample or other substance has been collected. Brush U.S. Pat. No. 4,150,666 discloses a blood collection tube holder having a substantially tubular body open at one end to receive and guide a collection tube as it moves thereinto. The opposite end of the tubular body is closed by a wall in which a double-ended needle cannula is positioned. One end of the needle projects outwardly from the end wall of the holder for insertion into a patient's blood vessel while the opposite end of the needle extends axially in the tube holder and is positioned to penetrate the stopper on the sample tube and establish fluid communication with the interior of the collection or sample tube. With the known constructions, however, it is often necessary to draw a number of blood samples for different tests from the same patient while maintaining the same tube holder needle in the vein of the patient to avoid subjecting the patient to multiple punctures. Recently the use of relatively small blood collection tubes, such as 10 millimeter tubes which accommodate samples of two to four milliliters in volume, has been preferred and has become common practice due to the small sample sizes required for many of the blood tests most frequently performed. Other more extensive blood tests, however, may require larger samples and hence larger volume collection tubes and difficulties can occur if the same tube holder is used with tubes of widely differing sizes. Furthermore, the technician may find it difficult to maintain a holder, sized for a relatively large collection tube, steady and the double-ended needle in the patient's vein while trying to penetrate the center portion of a smaller tube stopper with the opposite end of the same needle. Also, failure to properly align the needle with the center portion of the small tube stopper can result in occluding or blocking the end of the double-ended needle in the stopper side wall. Still further, use of relatively small collection tubes with small stoppers approximating the diameter of the tube makes it difficult for laboratory personnel to remove the stopper without getting blood or serum on their fingers. This can make the handling hazardous especially when samples may contain infectious agents, such as hepatitis or AIDS virus. Therefore, it is desired to avoid such difficulties while at the same time being able to employ a single tube holder for collecting several blood samples in collection tubes of differing sizes.

The present construction overcomes these and other problems associated with the known prior art and includes a tube holder designed to guide the collection tube and its stopper so that the end portion of the needle in the holder device will penetrate a central thinner diaphragm portion of the stopper and move through the stopper diaphragm to communicate with the interior of the sample tube, thus avoiding the possibility of moving the open end of the needle against the side wall of the stopper or of the sample tube and blocking or occluding the needle. The present stopper construction is relatively inexpensive to make, is easy to use, can be used with containers of differing size and is relatively fail safe.

OBJECT OF THE INVENTION

It is therefore a primary object of the present invention to teach the construction and operation of a stopper for medical containers which avoids the above noted difficulties and shortcomings of the known prior art devices.

Another object is to provide a stopper that lends itself to use in relatively small size blood collection tubes and also enables such small collection tubes to be used with tube holders sized for use with larger collection tubes.

Another object is to provide a stopper for use with relatively small collection tubes which decreases the possibility of occluding or blocking the flow path through an open ended needle that is provided to penetrate the stopper.

A further object is to provide a stopper for blood collection tubes and like containers which can be relatively easily removed therefrom.

Another object is to teach the construction and operation of a relatively inexpensive, easy to use stopper for use on devices such as blood collection tubes and the like.

Another object is to provide a versatile stopper that facilitates obtaining one or more blood samples from a patient while subjecting the patient to minimal discomfort and body punctures.

Another object is to make it easier and more reliable to take blood samples from patients.

A still further object is to provide a stopper for collection tubes such as blood sample collection tubes which reduces the possibility of the user coming in contact with the contents thereof.

These as well as other objects and advantages of the present invention will become apparent to those skilled in the art from the following detailed description and accompanying drawing of a preferred embodiment, wherein:

BRIEF DESCRIPTION OF THE DRAWING

FIG. 1 is a cross-sectional view through the center of a stopper constructed in accordance with the teachings of the present invention;

FIG. 2 is a bottom view of the stopper as shown in FIG. 1;

FIG. 3 is a top view of the stopper shown shown in FIG. 1;

FIG. 4 is a side view showing the stopper of FIG. 1 mounted in the open end of a collection tube; and FIG. 5 is an enlarged cross-sectional view showing the stopper-tube assembly of FIG. 4 inserted into a tube holder having a needle mounted thereon in position such that the stopper will be pierced and penetrated by one end of the needle.

DESCRIPTION OF THE PREFERRED EMBODIMENT

Referring to the drawing more particularly by reference numbers, FIG. 1 shows a stopper 10 constructed according to the present invention. The stopper 10 is shown as being of unitary construction having an annular flange portion 12 and a smaller diameter tube-closing plug portion 14. The flange portion 12 has an end face 16 which includes a centrally located depression or well 18 defined by tapered side and bottom surfaces 20 and 22 respectively. The flange 12 also has a frusto-conical outer surface 24 which extends from the end face 16 to its opposite end where it meets the outer periphery of radial face 26. The flange portion 12 is larger in diameter than the plug portion 14 by a substantial factor typically by a factor of from about 1.4 to about 2.0 times. A preferred ratio of these diameters is about 1.7. This preferred ratio enables a standard 10 millimeter collection tube to be used with a standard needle holder device having an inside diameter of from about 0.665 inch to 0.720 inch. At the juncture of flange and plug portions 12 and 14 an annular inwardly extending groove 28 is formed which enables the portions 12 and 14 to move angularly relative to each other to some extent thereby facilitating inserting and removing the plug portion 14 into a container or collection tube as will be described.

The plug portion 14 is formed by an annular wall 30 which has an outer surface 32 that preferably has a slight end-to-end taper as shown to enable the plug portion 14 to be relatively easily and sealably inserted into the open end 34 of a container 36 such as the container shown in FIGS. 4 and 5. The stopper 10 is preferably constructed of a relatively resilient material such as rubber or rubber like composition including thermoset rubbers such as butyl rubber, bromobutyl rubber, styrene butadiene rubber, nitrile butadiene rubber as well as thermoplastic rubbers such as polyester elastomer, styrene-base elastomer, polybutadiene or polyolyfin elastomer so that there is some give and compression of the plug portion 14 as it is inserted. Any of the commonly used lubricating agents and mold release agents are suitable for use with the particular rubber composition selected to be used. Also, additives can be employed in the stopper such as dyes, pigments, hemorepellants, and the like. It is also contemplated to have the free end of the plug portion 14 formed with an optional reduced diameter groove 37 to facilitate inserting the plug portion 14 into open end 34 of the container 36.

The plug portion 14 is annular in shape and has an inside surface 38 which terminates in a bottom or end surface 40 as clearly shown in FIG. 1. The bottom or end surface 40 is spaced from the bottom surface 22 of recess or well 18 formed in the end surface of the flange portion 12, and it is preferred that the surface 22 which forms the bottom of the well 18 be at least as large in area, and preferably somewhat larger, than the area of the bottom surface 40 of recess 44 in the plug portion 14. The portion 46 of the stopper 10 between the surfaces 22 and 40 can be referred to as the diaphragm portion of the stopper 10, and is the portion through which a needle or other piercing instrument projects when the device is to be used to receive a blood or other sample during operation of the device as will be described more fully hereinafter.

In FIG. 4, the stopper 10 is shown mounted in the open end 34 of the tubular container 36 which container may be a small sample container or test tube. The container 36 has a side wall 48 which is shown as tubular in shape terminating in a closed end wall 50. The inner surface 52 of the container 36 is sized to slidably and sealably receive the plug portion 14 of the stopper 10 when the stopper is pressed or twisted therein. The stopper 10 is usually pressed into the open end 34 of the container 36 until the end 54 of the container bears against the surface 26 on the flange portion 12 of the stopper. Insertion of the plug portion 14 into the container can take place during manufacture in which case the stopper and the container including especially the interior of the container are sterilized and may be partially evacuated leaving a vacuum condition therein. Furthermore, the stopper 10 should not be so tight-fitting in the container 36 as to be difficult to remove since the stopper may be required to be removed by a technician or other person in order to extract the blood or other sample contained therein for some purpose, although it is also contemplated to remove the sample by means of another needle on an extraction device. Removal of the stopper 10 from the container 36 is facilitated by having the flange portion 12 relatively large in diameter for ease of grasping and twisting. By having the flange portion relatively large and easy to grasp it effectively isolates the open end 34 of the container 36 from the fingers of the remover. Also, the larger flange portion makes it less likely that the person removing the stopper will lose control and spill the contents including spilling the contents onto his or her skin or clothing.

The subject stopper, and the container in which it is installed, are designed to be used in association with a holder device such as the holder device 56 as shown in FIG. 5. The holder device 56 is shown including an elongated tubular portion 58 closed at one end by wall 60 and having an outwardly extending flange portion 62 at the opposite end. The closed end wall 60 has a central portion 64 which supports a double ended needle member 66 which is shown having a portion 68 extending inside the holder 56 and a portion 70 extending from the end of the holder. Both ends 72 and 74 of the needle 66 are open and both are tapered as shown to facilitate their penetration into the stopper or into skin of a patient with which they come in contact.

The tubular portion 58 of the holder 56 has a cylindrical inner surface 76 which is sized to slidably receive the tapered flanged portion 12 of the stopper 10 when the stopper and the container on which it is installed are inserted into the holder 56 as shown in FIG. 5. Ideally the container 36 and the holder 56 should be in axial alignment when the container is inserted but this may not always be the case especially when the insertion is made while the end portion 70 of the needle 66 is inserted into the vein of a patient from whom a blood sample is being removed. It is important to the operation of the present device however, that whether the members 36 and 56 are in precise axial alignment or not that the inner end portion 68 of the needle 66 engage and pierce the diaphragm portion 46 of the stopper 10 and in so doing will pass therethrough and enter the container 36 somewhere in the region defined within the cavity or plug well portion 44 . In other words, regardless of the angle at which the needle portion 68 engages and pierces the stopper 10 it should not be possible for the needle to pierce the stopper so as to penetrate the annular portion 30 of the plug portion 14. This assures that the piercing end 72 of the needle 66 will never be blocked or occluded when a blood sample is being taken from the vein or artery of a patient. This is especially important when using small diameter collection tubes since the likelihood of blocking or occluding the end 72 of needle 66 increases substantially when relatively small collection containers or tubes are used with correspondingly small stoppers, such, for example, as 10 millimeter blood collection tubes in holders that are constructed to accomodate larger collection tubes such as 16 millimeter collection tubes.

In a typical application a single holder device 56 is therefore able to receive different size collection tubes even while the opposite end portion 70 of the needle 66 remains inserted into a patient's vein. This means that once the needle has been inserted into a vein the containers into which the blood being drained is collected can be changed in order to allow the blood to flow into several different containers from the patient. Furthermore, changing from one size container to another can be accomplished with minimal blood loss and with minimal possibility that the blood being taken will come into contact with the technician, doctor, or nurse performing the procedure. These are important considerations and mean that blood samples of different sizes can be taken from the same patient without having to reinsert the needle into the patient for each sample and without causing the patient additional discomfort. The construction of the present stopper also protects against the one taking the samples piercing the stopper in a manner which will obstruct the blood flow, and this is true regardless of the angle at which the container is inserted into the holder device. All of these are important features and advantages and ones which are available when using the present construction.

In a typical situation it has been found that the outside diameter at the widest point on the flange 12 should be between about 1.4 and about 2.0 times the diameter of the plug portion 14 at its widest point, and the surface 22 should be substantially larger than the surface 40, and should be such as to assure that the needle will be properly located to penetrate the stopper regardless of the various possible angles of the container 36 when inserted into the holder 56. In the case of a typical 10 millimeter blood collection tube having an inside diameter of about 9.85 millimeters, the outside diameter of the flange portion 12 should be in the range from about 1.6 to about 1.8 times the inside diameter of the collection tube 36, i.e. from about 15.8 to about 18.0 millimeters, and preferably between about 16.8 to 17.8 millimeters. Such dimensions assure proper guidance and alignment of the collection tube 36 fitted with such a stopper 10 and the successful penetration of the needle portion 68 into and through the diaphram portion 46 of the stopper. It should also be noted that as the diameter of the collection tube becomes smaller in relation to the diameter of the holder 56 there is a greater chance for trouble when using the device. This is especially true when inserting a 10 millimeter collection tube into a standard holder which has an inside diameter of about 0.720 inch at the open end thereof.

Not only is the alignment of the needle an important consideration, particularly when using relatively small diameter containers and stoppers, but if the point at which the needle 66 initially penetrates is in a sloping wall portion of the stopper as for example in wall portion 20, it may develop what is known as "point roll" which is a condition that tends to deflect the needle sidewardly and outwardly toward the side wall 30 of the plug portion 14. If a relatively thin-walled needle of small guage is used, "point rolling" may deflect an originally straight needle to such an extent that the free end thereof engages the wall 30 and is blocked or becomes occluded or moves into the side wall 30 of the plug portion 14. Any of these conditions can produce a "no vacuum" effect and prevent or at least discourage movement of the blood from the patient into the collection tube 36. Such a condition may also require that the container 36 be withdrawn from the holder so that the needle will be withdrawn to enable another penetration to take place before the device will operate properly. The possibility of "point roll" is further obviated in the present construction by having the bottom wall portion 22 of the outer recess or well 18 made relatively large and flat so that the needle will not be as likely to attempt to enter at a sloping wall portion of the stopper. Consequently, the "point roll" condition is largely overcome by the construction of the present stopper.

It should also be kept in mind that with the present construction the amount of possible angular movement between the stopper 10 and the holder member 56 into which it is positioned is limited by the size and shape of the collection tube 36 and to some extent by the length of the collection tube. The important thing is that the varied possible angular positioning of the stopper be such that the needle will never be able to enter the stopper so as to produce the undesirable conditions set forth above.

Thus there has been shown and described a novel stopper construction for use with medical containers, and especially with blood collection tubes and the like which fulfills all of the objects and advantages sought therefor. It will be apparent to those skilled in that art, however, that many changes, modifications, variations, and other uses and applications for the subject stoppers are possible and contemplated. All such changes, modifications, variations, and other uses and applications which do not depart from the spirit and scope of the invention are deemed to be covered by the invention which is limited only by the claims which follow.

What is claimed is:

1. In combination, a tube having an opening, a stopper for closing the opening in said tube, and a holder for said tube and stopper, comprising:

a holder body closed at one end and open at an opposite end with an axially extending hollow needle positioned therein such that one end of said needle extends into said holder body toward said opening and an opposite end of said needle extends outside said holder body, a hollow elongated blood collection tube having a tubular side wall portion terminating at one end of said tube in a closed end wall portion and having a round in diameter open end opposite the closed end wall portion of said tube, a stopper body having round and connected flange and plug portions, the flange portion of said stopper body being substantially larger in diameter than the plug portion of said stopper body and sized to be slidably moved into the holder body and against the needle end extending into said holder body, the largest diameter of the flange portion of said stopper body exceeding the largest diameter of the sidewall portion of said tube proximate the opening in said tube by a factor of at least 1.4 and, means forming aligned and opposed cavities in the flange and plug portions defining a relatively thin diaphragm portion therebetween.

2. The tube, stopper and holder combination of claim 1 wherein the largest diameter of the flange portion of said stopper body exceeds the largest diameter of the portion of said tube proximate the opening in said tube by a factor of from about 1.4 to about 2.0 times.

3. The tube stopper and holder combination of claim 1 adapted for use on a 10 millimeter tube, wherein the largest diameter of the flange portion of said stopper body exceeds the largest diameter of the portion of said tube proximate the opening in said tube thereof by a factor of about 1.7 times.

4. The tube, stopper and holder combination of claim 1 wherein the diameter of the flange portion of said stopper body is sufficiently large to prevent misalignment of the diaphragm portion of said stopper body with the axis of said needle when said tube with said stopper body inserted in the open end of said tube is positioned stopper first within the open end of said holder body, irrespective of the angle of orientation of said tube with respect to said needle.

5. A medical blood collection kit comprising in combination:
a holder body closed at one end and open at an opposite end with an axially extending hollow needle positioned therein such that one end of said needle extends into said holder body toward said open end and an opposite end of said needle extends outside said holder body,
at least one small blood collection tube and stopper combination formed by a hollow elongated small diameter tube having a tubular side wall portion terminating at one end of said small tube in a closed end wall portion and having a round in diameter open end opposite the closed end wall portion of said small tube, and a small stopper having connected flange and plug portions, the flange portion of said small stopper being larger in diameter than the plug portion of said small stopper and sized to be slidably moved into the holder body and against the needle end extending into said holder body, the largest diameter of the flange portion of said small stopper exceeding the largest diameter of the portion of said small tube proximate the open end in said small tube by a factor of at least 1.4; and
at least one large blood collection tube and stopper combination formed by a hollow elongated large diameter tube having a tubular side wall portion terminating at one end of said large tube in a closed end wall portion and having a round in diameter open end opposite the closed end wall portion of said large tube, a large stopper having connected flange and plug portions, the flange portion of said large stopper being substantially larger in diameter than the plug portion and sized to be slidably moved into the holder body and against the needle end extending into said holder body, the largest diameter of the flange portion of said large stopper exceeding the largest diameter of the portion of said large tube proximate the open end in said large tube by a factor of less than 1.4.

6. The medical blood collection kit of claim 5 wherein the outside diameter of said small tube of said at least one small tube and stopper combination is not more than 12 millimeters and the outside diameter of said large tube of said at least one large tube and stopper combination is at least 14 millimeters.

7. A method for collecting blood from an animal body comprising the steps of:
providing a blood collection tube holder in the form of a hollow holder body having an open end, and a needle mounted on said holder body opposite the open end of said holder body, with one end of said needle extending into said holder body toward the open end of said holder body,
inserting an other end of said needle opposite said one end of said needle into a blood vessel of an animal body,
communicating blood from said vessel through a bore of said needle to said one end of said needle,
providing at least one large diameter blood collection tube and at least one smaller diameter blood collection tube, each tube having a stopper closure for closing an open end of said respective tube, each stopper having a plug portion adapted to fit within an open end of each said tube and a flange portion extending out of each said tube, the flange portion of each of said stoppers having approximately the same functional diameter corresponding to an inside diameter of said holder body, and said blood collection tubes having a predetermined outside diameter such that the diameter of the flange portion of said stopper is at least 1.4 times the outside diameter of the smaller diameter tubes and not more than 1.4 times the outside diameter of the larger diameter tubes,
positioning one of the larger diameter tubes stopper first into the open end of said holder body, and advancing said larger diameter tube within the holder body until the one end of said needle pierces the stopper of said larger diameter tube, then withdrawing the tube from the holder after a blood sample has collected in the tube, and
positioning one of the smaller diameter tubes stopper first into the open end of said holder body, and advancing said small diameter tube within said holder body until the one end of said needle pierces the stopper of said smaller tube, then withdrawing the smaller tube from the holder after a blood sample has collected in the smaller tube.

8. A method for collecting blood from an animal body in two different-sized blood collection tubes comprising the steps of:
providing a hollow collection tube holder having an open end, a minimum inside holder diameter and a double ended needle mounted opposite and in alignment with the open end of said holder,
providing at least one large blood collection tube having an outside large tube diameter slightly smaller than the holder diameter and closed by a large tube stopper having a flange portion, said flange portion having a diameter at most slightly larger than the tube diameter,
providing at least one small blood collection tube having an outside small tube diameter at most substantially smaller than the holder diameter and closed by a small tube stopper having a flange portion, said flange portion having a diameter at least substantially larger than the small tube diameter,
communicating the needle with a blood vessel of an animal body; then using said holder, inserting one of the large tubes stopper first into the open end of the holder,
pushing the large tube into the holder until the needle pierces the stopper and blood flows into the large tube, withdrawing the large tube from the holder when a desired sample is collected; and
inserting one of the small tubes stopper first into the open end of the holder,
pushing the small tube into the holder until the needle pierces the stopper and blood flows into the small tube,
withdrawing the small tube from the holder when a desired sample is collected.

* * * * *